(12) United States Patent
Fache

(10) Patent No.: US 7,705,179 B2
(45) Date of Patent: Apr. 27, 2010

(54) METHOD FOR OXIDISING HYDROCARBONS, ALCOHOLS AND/OR KETONES

(75) Inventor: Eric Fache, Caluire et Cuire (FR)

(73) Assignee: Rhodia Polyamide Intermediates, Saint Fons (FR)

( * ) Notice: Subject to any disclaimer, the term of this patent is extended or adjusted under 35 U.S.C. 154(b) by 1840 days.

(21) Appl. No.: 10/312,534

(22) PCT Filed: Jun. 22, 2001

(86) PCT No.: PCT/FR01/01976

§ 371 (c)(1), (2), (4) Date: Jun. 2, 2003

(87) PCT Pub. No.: WO02/00588

PCT Pub. Date: Jan. 3, 2002

(65) Prior Publication Data

US 2005/0277787 A1    Dec. 15, 2005

(30) Foreign Application Priority Data

Jun. 28, 2000 (FR) .................................. 00 08323

(51) Int. Cl.
 *C07C 51/16* (2006.01)
 *C07C 51/31* (2006.01)
(52) U.S. Cl. ...................................... 562/543; 562/542
(58) Field of Classification Search .................. 562/542, 562/543
See application file for complete search history.

(56) References Cited

U.S. PATENT DOCUMENTS

| | | | | |
|---|---|---|---|---|
| 2,223,493 A | * | 12/1940 | Loder | 562/543 |
| 2,844,626 A | * | 7/1958 | Kamlet | 562/540 |
| 6,787,669 B1 | * | 9/2004 | Costantini et al. | 562/543 |

FOREIGN PATENT DOCUMENTS

| | | | |
|---|---|---|---|
| EP | 0 784 045 A | | 7/1997 |
| EP | 0824962 | * | 2/1998 |
| EP | 0 870 751 A | | 10/1998 |
| FR | 2 775 685 A | | 9/1999 |
| WO | WO 00 15598 A | | 3/2000 |

* cited by examiner

*Primary Examiner*—Taylor Victor Oh
(74) *Attorney, Agent, or Firm*—Buchanan Ingersoll & Rooney PC

(57) ABSTRACT

The present invention relates to the oxidation with oxygen, or a gas containing it, of hydrocarbons to the corresponding carboxylic acids, alcohols and/or ketones or of alcohols and/or ketones to the corresponding carboxylic acids.

More specifically, the invention consists of a process for oxidizing hydrocarbon, alcohol and/or ketone using oxygen or a gas containing it, in a liquid phase and in the presence of a catalyst dissolved in the reaction medium, characterized in that the catalyst comprises at least one soluble manganese and/or cobalt compound, at least one soluble chromium compound and at least one soluble iron compound.

17 Claims, No Drawings

METHOD FOR OXIDISING HYDROCARBONS, ALCOHOLS AND/OR KETONES

The present invention relates to the oxidation with oxygen, or a gas containing it, of hydrocarbons to the corresponding carboxylic acids, alcohols and/or ketones or of alcohols and/or ketones to the corresponding carboxylic acids.

The direct oxidation with oxygen of hydrocarbons, more particularly of cycloalkanes, in the presence of a catalyst, is a process which has been studied for a long time. The reason for this is that there would be obvious advantages in avoiding the use of an oxidizing agent such as nitric acid, used in one of the steps of the current industrial processes, which would spare the need to process the nitrogen oxides generated.

In the many variants of such a process of catalytic oxidation with oxygen, cobalt is the catalyst most frequently recommended.

Thus, American patent U.S. Pat. No. 2,223,493, published in December 1940, describes the oxidation of cyclic hydrocarbons to the corresponding diacids, in a liquid phase generally comprising acetic acid, at a temperature of at least 60° C., using a gas containing oxygen and in the presence of an oxidation catalyst such as a cobalt compound.

American patent U.S. Pat. No. 4,902,827, published in February 1990, describes an improvement to the air oxidation of cyclohexane to adipic acid, in a liquid phase comprising acetic acid, at a temperature of from 80° C. to 160° C. and in the presence of an oxidation catalyst comprising a soluble cobalt compound and a soluble zirconium and/or hafnium compound.

More recently, it has been recommended in patent EP-A-0 694 333 to use, in the context of the oxidation of hydrocarbons with oxygen, a catalyst comprising a cobalt salt and a ferric salt.

It has also been recommended in patent EP 0 870 751 to use a catalyst comprising a cobalt salt and a chromium salt to improve the selectivity.

Another common catalyst for this oxidation reaction which may be mentioned is manganese.

For economic reasons but also to make the products obtained easier to purify, it is preferable to work with a catalyst concentration which is as low as possible. Thus, manganese is an advantageous catalyst in processes for oxidizing cyclohexane.

Nevertheless, it turns out that although the selectivities obtained with the catalytic systems used in the prior-art processes described above are acceptable, the production efficiency of these processes needs to be further improved in order to allow such a reaction to be exploited industrially.

This is what the present invention proposes to achieve. More specifically, the invention consists of a process for oxidizing hydrocarbon, alcohol and/or ketone using oxygen or a gas containing it, in a liquid phase and in the presence of a catalyst dissolved in the reaction medium, characterized in that the catalyst comprises at least one soluble manganese and/or cobalt compound, at least one soluble chromium compound and at least one soluble iron compound.

The hydrocarbons which are used as starting substrates in the process of the invention are more particularly alkanes, cycloalkanes, alkylaromatic hydrocarbons, alkenes and cycloalkenes containing from 3 to 20 carbon atoms.

Among these hydrocarbons, the cycloalkanes, in particular those which have a ring containing from 5 to 12 carbon atoms, are definitely the most important, since their oxidation leads to dicarboxylic acids or to the intermediate cycloalkanols and cycloalkanones.

The hydrocarbon which is most advantageous is cyclohexane, the oxidation of which leads to adipic acid, one of the base compounds of polyamide 6,6, but may also give cyclohexanone leading to caprolactam and thus to polyamide 6.

The present process may also be used for the oxidation of the intermediate alcohols or ketones, in particular cycloalkanols and cyclohexanones containing from 5 to 12 carbon atoms, to prepare the corresponding dicarboxylic acids.

In the text hereinbelow, the process will be described more particularly for the oxidation of hydrocarbons, essentially cycloalkanes, and preferably for the oxidation of cyclohexane.

The catalytic system comprising manganese and/or cobalt, chromium and iron compounds makes it possible to prepare adipic acid directly with good selectivity and improved production efficiency, when the oxidation of cyclohexane is performed. These catalytic properties are obviously very advantageous for an industrial exploitation of this oxidation reaction.

The catalytic system comprises either at least one manganese compound which is soluble in the reaction medium, chosen, for example, in a non-limiting manner, from manganese chloride, manganese bromide, manganese nitrate and manganese carboxylates, for instance manganese acetate tetrahydrate, manganese propionate, manganese adipate, manganese glutarate or manganese succinate, or at least one cobalt compound which is soluble in the reaction medium, chosen, for example, in a non-limiting manner, from cobalt chloride, cobalt bromide, cobalt nitrate and cobalt carboxylates, for instance cobalt acetate tetrahydrate, cobalt propionate, cobalt adipate, cobalt glutarate or cobalt succinate.

The catalyst also comprises at least one chromium compound which is soluble in the reaction medium, chosen, for example, in a non-limiting manner, from chromium chloride, chromium bromide, chromium nitrate and chromium carboxylates, for instance chromium acetate, chromium propionate, chromium adipate, chromium glutarate or chromium succinate, and mineral or organic chromic acid salts.

The catalyst also comprises at least one iron compound which is soluble in the reaction medium, chosen, for example, in a non-limiting manner, from iron halides, iron nitrate, iron carboxylates, for instance the acetate, propionate, succinate, glutarate or adipate, and iron chelates, for instance iron acetylacetonates.

Finally, the catalyst may also comprise at least one zirconium and/or hafnium compound which is soluble in the reaction medium, chosen, for example, in a non-limiting manner, from zirconium chloride, zirconium bromide, zirconium nitrate and zirconium carboxylates, for instance zirconium acetate, zirconium propionate, zirconium adipate, zirconium glutarate or zirconium succinate, and hafnium chloride, hafnium bromide, hafnium nitrate and hafnium carboxylates, for instance hafnium acetate, hafnium propionate, hafnium dipate, hafnium glutarate or hafnium succinate.

The molar ratios between the manganese and/or the cobalt, the chromium and the iron in the catalytic system may vary within a wide range. It is thus possible to use Mn and/or Co/Cr/Fe molar ratios which are advantageously between 1/0.00001/0.0001 and 1/100/100, preferably between 1/0.001/0.01 and 1/10/10.

The amount of zirconium or hafnium, when they are present, may vary in molar ratios, relative to the manganese or cobalt, which are similar to those indicated above for chromium.

The catalyst may be obtained in situ by loading the manganese and/or cobalt, chromium, iron and optionally zirconium or hafnium compounds into the reaction medium. It may also be prepared at the time of use by mixing the said compounds in the proportions required to obtain the desired Mn and/or Co/Cr/Fe and optionally Zr and/or Hf molar ratios. Preferably, this mixture is prepared using a solvent, advantageously a solvent of the same nature as the one used for the oxidation reaction or directly in this solvent.

The amount of catalyst, expressed as a weight percentage of metal elements (manganese, cobalt, chromium, iron and, optionally, zirconium or hafnium) relative to the reaction mixture, is generally between 0.0001% and 5% and advantageously between 0.001% and 2%, without these values being critical. Nevertheless, it is a case of having an activity which is sufficient without, however, using excessively large amounts. The reason for this is that the catalyst will have to be separated from the final reaction medium and recycled.

It is advantageous also to use a compound which initiates the oxidation reaction. The initiators are often hydroperoxides, for example cyclohexyl hydroperoxide or tert-butyl hydroperoxide. They are also ketones or aldehydes, for example cyclohexanone which is one of the compounds formed during the oxidation of cyclohexane or of acetaldehyde. Generally, the initiator represents from 0.01% to 20% by weight relative to the weight of the reaction mixture used, without these proportions having a critical value. The initiator is useful above all when starting the oxidation and when the oxidation of cyclohexane is performed at a temperature below 120° C. It may be introduced from the start of the reaction.

The liquid reaction medium preferably contains a solvent which is at least a partial solvent for the carboxylic acid and/or the alcohol and/or the ketone whose preparation is intended by carrying out the process of the invention. This solvent may be of very varied nature, provided it is not substantially oxidizable under the reaction conditions. It may be chosen in particular from polar protic solvents and polar aprotic solvents. Polar protic solvents which may be mentioned, for example, are carboxylic acids containing only primary or secondary hydrogen atoms, in particular aliphatic acids containing from 2 to 9 carbon atoms, perfluoroalkyl carboxylic acids such as trifluoroacetic acid, and alcohols such as tert-butanol. Polar aprotic solvents which may be mentioned, for example, are lower alkyl esters (=alkyl radical containing from 1 to 4 carbon atoms) of carboxylic acids, in particular of aliphatic carboxylic acids containing from 2 to 9 carbon atoms or of perfluoroalkylcarboxylic acids, tetramethylene sulphone (or sulpholane), acetonitrile, halogenated hydrocarbons such as dichloromethane, and ketones such as acetone.

Acetic acid is preferably used as solvent for the oxidation reaction of cyclohexane. It is convenient to use a catalyst whose manganese and chromium constituents are in the form of compounds derived from the carboxylic acid used as solvent, provided that the said compounds are soluble in the reaction medium. Manganese acetate, chromium acetate and iron acetate are thus preferably used, in particular for this reason.

The solvent, as defined above, generally represents from 1% to 99% by weight of the reaction medium, preferably from 10% to 90% and even more preferably from 20% to 80%.

The oxidation may also be carried out in the presence of water introduced from the initial stage of the process.

The temperature at which the oxidation reaction is carried out is variable, in particular depending on the substrate used. It is generally between 50° C. and 200° C., and preferably between 80° C. and 140° C.

The pressure is not a critical parameter of the process. It may be less than, equal to or greater than atmospheric pressure. It will generally be between 0.1 MPa (1 bar) and 20 MPa (200 bar), without these values being imperative.

Pure oxygen, air, oxygen-enriched air, oxygen-depleted air or oxygen diluted with an inert gas may be used.

The examples which follow illustrate the invention.

EXAMPLE 1

The reagents below are loaded into a 1.5 l titanium autoclave equipped with heating means via a heating collar, cooling means, a turbomixer and means for introducing and removing gas and for pressure regulation, the autoclave being purged beforehand with nitrogen:

292.5 g of cyclohexane
357 g of acetic acid
3.4 g of cyclohexanone
4.16 g (16.7 mmol of Co) of cobalt acetate tetrahydrate
0.162 g (0.74 mmol of Cr) of chromium acetate dihydrate
1.183 g (3.2 mmol of Fe) of iron acetylacetonate
0.8 g of water.

After closing the reactor, it is stirred at 1000 rpm, a nitrogen pressure of 20 bar is created at 20° C. and heat is applied. The temperature reaches 105° C. in the bulk over 20 min. The nitrogen is replaced with air containing 5% oxygen under a pressure of 20 bar. The normal gas flow rate of the air is 250 l/h. After a brief period of about a few minutes without consumption of oxygen, the temperature rises by a few degrees and oxygen consumption is observed. The oxygen content of the air is gradually increased to a value of 21%. The oxygen content in the gas leaving the reactor remains less than 5%.

After reaction for 76 minutes, 52.8 normal liters of oxygen have been consumed, corresponding to a degree of conversion of the cyclohexane of about 20%.

After stopping the flushing with air and cooling to a temperature of 70° C., the reaction mixture is analysed to determine the degree of conversion and the selectivity. These analyses are performed by gas chromatography (the term "selectivity"—ST—means the molar ratio, expressed as a percentage of the number of moles metered, of a species relative to the theoretical number of moles of the species calculated from the number of moles of cyclohexane effectively converted).

The following results are obtained:

| | |
|---|---|
| Degree of conversion (DC) of the cyclohexane: | 20.7% |
| ST of cyclohexanol relative to the cyclohexane converted: | 6.3% |
| ST of cyclohexanone relative to the cyclohexane converted: | 4.9% |
| ST of adipic acid relative to the cyclohexane converted: | 67.1% |
| ST of adipic acid + cyclohexanone + cyclohexanol relative to the cyclohexane converted: | 78.3% |
| Molar ratio of adipic acid/total diacids formed: | 85.9% |

EXAMPLE 2—COMPARATIVE

Example 1 is repeated in the same apparatus and under the same operating conditions, loading the following reagents:

292.5 g of cyclohexane
357 g of acetic acid
3.4 g of cyclohexanone
4.0 g (16.2 mmol of Co) of cobalt acetate tetrahydrate
0.157 g (0.64 mmol of Cr) of chromium acetate dihydrate
0.6 g of water.

The reaction time is 95 minutes instead of 76 minutes in Example 1, for an equivalent degree of conversion.

The following results are obtained:

| | |
|---|---|
| Degree of conversion (DC) of the cyclohexane: | 21.1% |
| ST of cyclohexanol relative to the cyclohexane converted: | 5.1% |
| ST of cyclohexanone relative to the cyclohexane converted: | 3.4% |
| ST of adipic acid relative to the cyclohexane converted: | 70.9% |
| ST of adipic acid + cyclohexanone + cyclohexanol relative to the cyclohexane converted: | 79.4% |
| Molar ratio of adipic acid/total diacids formed: | 85.7% |

This test clearly shows the influence of the iron on the activity of the catalyst. Specifically, in order to obtain a similar degree of conversion of the cyclohexane, the reaction time was 25% shorter in Example 1, while maintaining an equivalent selectivity towards adipic acid.

EXAMPLE 3—COMPARATIVE

Example 1 is repeated in the same apparatus and under the same operating conditions, loading the following reagents:
  292.5 g of cyclohexane
  357 g of acetic acid
  3.4 g of cyclohexanone
  4.17 g (16.7 mmol of Co) of cobalt acetate tetrahydrate
  0.8 g of water.
The reaction time is 75 minutes.
The following results are obtained:

| | |
|---|---|
| Degree of conversion (DC) of the cyclohexane: | 20.3% |
| ST of cyclohexanol relative to the cyclohexane converted: | 11.6% |
| ST of cyclohexanone relative to the cyclohexane converted: | 4.5% |
| ST of adipic acid relative to the cyclohexane converted: | 61.9% |
| ST of adipic acid + cyclohexanone + cyclohexanol relative to the cyclohexane converted: | 78.2% |
| Molar ratio of adipic acid/total diacids formed: | 85.4% |

This test shows, in comparison with Example 1, the positive effect of the presence of iron and chromium on the selectivity and production efficiency of the catalyst.

EXAMPLE 4

Example 1 is repeated in the same apparatus and under the same operating conditions, but loading the following compounds into the reactor:
  292.5 g of cyclohexane
  357 g of acetic acid
  3.4 g of cyclohexanone
  4.13 g (16.6 mmol of Co) of cobalt acetate tetrahydrate
  0.2325 g (1.06 mmol of Cr) of chromium acetate dihydrate
  1.086 g (3.1 mmol of Fe) of iron acetylacetonate
  0.8 g of water.
The reaction time is 73 minutes.
The following results are obtained:

| | |
|---|---|
| Degree of conversion (DC) of the cyclohexane: | 20.3% |
| ST of cyclohexanol relative to the cyclohexane converted: | 9.8% |
| ST of cyclohexanone relative to the cyclohexane converted: | 2.5% |
| ST of adipic acid relative to the cyclohexane converted: | 68.8% |
| ST of adipic acid + cyclohexanone + cyclohexanol relative to the cyclohexane converted: | 78.3% |
| Molar ratio of adipic acid/total diacids formed: | 85.3% |

EXAMPLE 5—COMPARATIVE

Example 1 is repeated in the same apparatus and under the same operating conditions, but loading the following compounds into the reactor:
  292.5 g of cyclohexane
  357 g of acetic acid
  3.4 g of cyclohexanone
  4.0 g (16.1 mmol of Co) of cobalt acetate tetrahydrate
  0.309 g (1.25 mmol of Cr) of chromium acetate dihydrate
  0.6 g of water.
The reaction induction time is 50 minutes and the reaction time is 160 minutes.
The following results are obtained:

| | |
|---|---|
| Degree of conversion (DC) of the cyclohexane: | 17% |
| ST of cyclohexanol relative to the cyclohexane converted: | 4.6% |
| ST of cyclohexanone relative to the cyclohexane converted: | 1.7% |
| ST of adipic acid relative to the cyclohexane converted: | 74.3% |
| ST of adipic acid + cyclohexanone + cyclohexanol relative to the cyclohexane converted: | 77.2% |
| Molar ratio of adipic acid/total diacids formed: | 83.4% |

This test taken in comparison with Example 4 clearly shows the positive effect on the production efficiency of the combination of iron with chromium, without significantly affecting the selectivity.

EXAMPLE 6

The reagents below are loaded into a 1.5 l titanium autoclave equipped with heating means via a heating collar, cooling means, a turbomixer and means for introducing and removing gas and for pressure regulation, the autoclave being purged beforehand with nitrogen:
  292.5 g of cyclohexane
  357 g of acetic acid
  3.67 g of cyclohexanone
  4.13 g (16.6 mmol of Co) of cobalt acetate tetrahydrate
  0.1595 g (0.73 mmol of Cr) of chromium acetate dihydrate
  1.0895 g (3.1 mmol of Fe) of iron acetylacetonate
  0.8 g of water.
After closing the reactor, it is stirred at 1000 rpm, a nitrogen pressure of 20 bar is created at 20° C. and heat is applied. The temperature reaches 105° C. in the bulk over 20 min. The nitrogen is replaced with air containing 5% oxygen under a pressure of 20 bar. The normal gas flow rate of the air is 250 l/h. After a brief period of about a few minutes without consumption of oxygen, the temperature rises by a few degrees and oxygen consumption is observed. The oxygen content of the air is gradually increased to a value of 21%. The oxygen content in the gas leaving the reactor remains less than 5%.

When 50 normal liters of oxygen have been consumed, corresponding to a degree of conversion of the cyclohexane of about 20%, continuous injection into the liquid phase of a solution of acetic acid containing 1.1% by weight of cobalt acetate tetrahydrate, 0.043% by weight of chromium acetate dihydrate and 0.3% by weight of iron acetylacetonate at a flow rate of 3.9 ml/min and an injection of 4.3 ml/min of cyclohexane are begun.

The consumption of oxygen during the injection period is 0.6 l/min.

After stopping the flushing with air and stopping the injections of the reagents, the mixture is cooled to a temperature of 70° C. The reaction mixture is analysed to determine the various degrees of conversion and selectivity. These analyses are performed by gas chromatography.

The following results are obtained:

| | |
|---|---|
| Degree of conversion (DC) of the cyclohexane: | 19.6% |
| ST of cyclohexanol relative to the cyclohexane converted: | 6.5% |
| ST of cyclohexanone relative to the cyclohexane converted: | 6.0% |
| ST of adipic acid relative to the cyclohexane converted: | 65.3% |
| ST of adipic acid + cyclohexanone + cyclohexanol relative to the cyclohexane converted: | 77.8% |
| Molar ratio of adipic acid/total diacids formed: | 85.1% |

The production efficiency of the catalyst is 60.7 g of adipic acid produced per liter and per hour.

EXAMPLE 7—COMPARATIVE

Example 6 is repeated in the same apparatus and under the same operating conditions, but eliminating only the iron in the initial load and in the solution injected.

The oxygen consumption during the injection period is 0.44 l/min.

The following results are obtained:

| | |
|---|---|
| Degree of conversion (DC) of the cyclohexane: | 18.2% |
| ST of cyclohexanol relative to the cyclohexane converted: | 5.1% |
| ST of cyclohexanone relative to the cyclohexane converted: | 4.8% |
| ST of adipic acid relative to the cyclohexane converted: | 69.5% |
| ST of adipic acid + cyclohexanone + cyclohexanol relative to the cyclohexane converted: | 79.4% |
| Molar ratio of adipic acid/total diacids formed: | 85.0% |

The production efficiency of the catalyst is 47.5 g of adipic acid produced per liter and per hour.

EXAMPLE 8—COMPARATIVE

Example 7 is repeated in the same apparatus and under the same operating conditions, but eliminating the iron and chromium in the initial load and in the solution injected.

The oxygen consumption during the injection period is 0.55 l/min.

The following results are obtained:

| | |
|---|---|
| Degree of conversion (DC) of the cyclohexane: | 18.5% |
| ST of cyclohexanol relative to the cyclohexane converted: | 10.8% |
| ST of cyclohexanone relative to the cyclohexane converted: | 5.8% |
| ST of adipic acid relative to the cyclohexane converted: | 61.6% |
| ST of adipic acid + cyclohexanone + cyclohexanol relative to the cyclohexane converted: | 78.2% |
| Molar ratio of adipic acid/total diacids formed: | 84.0% |

The production efficiency of the catalyst is 56.5 g of adipic acid produced per liter and per hour.

EXAMPLE 9—COMPARATIVE

The ingredients below are loaded into a 125 ml titanium autoclave equipped with heating means via a heating collar, a turbomixer and gas introduction and pressure regulation means:

21.25 g (253 mmol) of cyclohexane
27.35 g of acetic acid
0.26 g (2.65 mmol) of cyclohexanone
0.0357 g (0.146 mmol of Mn) of manganese acetate tetrahydrate
0.011 g of chromium acetate dihydrate (0.04 mmol of Cr).

After closing the reactor, it is stirred at 1000 rpm, an air pressure (100 bar at 20° C.) is created and the reactor is heated. The temperature reaches 105° C. in the bulk in 10 min and this temperature is maintained for a further 150 min.

After cooling and depressurization, the reaction mixture consists of two liquid phases, which are homogenized by adding acetic acid.

The homogeneous mixture thus obtained is assayed by gas chromatography.

The following results are obtained:

| | |
|---|---|
| Degree of conversion (DC) of the cyclohexane: | 14.9% |
| ST of cyclohexanol relative to the cyclohexane converted: | 19.4% |
| ST of cyclohexanone relative to the cyclohexane converted: | 0.0% |
| ST of adipic acid relative to the cyclohexane converted: | 50% |
| ST of adipic acid + cyclohexanone + cyclohexanol relative to the cyclohexane converted: | 69.4% |
| Molar ratio of adipic acid/total diacids formed: | 77.6% |

EXAMPLE 10

Example 9 is repeated, but using as catalytic system the system having the following composition:

0.3107 g (1.247 mmol of Co) of cobalt acetate tetrahydrate
0.0119 g (0.012 mmol of Cr) of chromium acetate dihydrate
0.0861 g (0.244 mmol of Fe) of iron acetylacetonate
0.0525 g (0.149 mmol of Mn) of manganese (III) acetylacetonate.

The mixture is maintained at 105° C. for 45 minutes.
The following results are obtained:

| | |
|---|---|
| Degree of conversion (DC) of the cyclohexane: | 12.1% |
| ST of cyclohexanol relative to the cyclohexane converted: | 9.5% |
| ST of cyclohexanone relative to the cyclohexane converted: | 8.1% |
| ST of adipic acid relative to the cyclohexane converted: | 67% |
| ST of adipic acid + cyclohexanone + cyclohexanol relative to the cyclohexane converted: | 85.6% |
| Molar ratio of adipic acid/total diacids formed: | 85.5% |

EXAMPLE 11

Example 10 is repeated, but using as catalytic system the system having the following composition:

0.3135 g (1.258 mmol of Co) of cobalt acetate tetrahydrate
0.0114 g (0.0113 mmol of Cr) of chromium acetate dihydrate
0.0828 g (0.234 mmol of Fe) of iron acetylacetonate
0.0522 g (0.148 mmol of Mn) of manganese (III) acetylacetonate
0.0059 g (0.0121 mmol of Zr) of zirconium acetylacetonate.

The following results are obtained:

| | |
|---|---|
| Degree of conversion (DC) of the cyclohexane: | 11.7% |
| ST of cyclohexanol relative to the cyclohexane converted: | 8.8% |
| ST of cyclohexanone relative to the cyclohexane converted: | 9.4% |
| ST of adipic acid relative to the cyclohexane converted: | 67.4% |

-continued

| | |
|---|---|
| ST of adipic acid + cyclohexanone + cyclohexanol relative to the cyclohexane converted: | 85.6% |
| Molar ratio of adipic acid/total diacids formed: | 85.7% |

The invention claimed is:

1. A process for producing a carboxylic acid which comprises oxidizing a compound selected from the group consisting of a cycloalkane, cycloalkanol and cycloalkanone, said compound having from 3 to 20 carbon atoms, with oxygen or a gas comprising oxygen, in a liquid phase in a solvent selected from the group consisting of polar protic solvents and polar aprotic solvents and in the presence of a catalyst dissolved in the reaction medium, at a temperature of about 50° C. to 200° C. and a pressure of about 0.1 MPa and 20 MPa, wherein the catalyst comprises: (1) at least one soluble manganese and/or cobalt compound, (2) at least one soluble chromium compound and (3) at least one soluble iron compound, wherein the molar ratios between the manganese and/or cobalt, the chromium and the iron are between 1/0.00001/0.0001 and 1/100/100.

2. The process according to claim 1, wherein the compound is a cycloalkane having a ring of from 5 to 12 carbon atoms.

3. The process according to claim 1, wherein the compound is selected from the group consisting of cycloalkanols and cycloalkanones having from 5 to 12 carbon atoms.

4. The process according to claim 1, wherein the at least one manganese compound soluble in the reaction medium is selected from the group consisting of manganese chloride, manganese bromide, manganese nitrate and manganese carboxylates.

5. The process according to claim 1, wherein the at least one cobalt compound soluble in the reaction medium is selected from the group consisting of cobalt chloride, cobalt bromide, cobalt nitrate, cobalt carboxylates, cobalt acetate, cobalt propionate, cobalt adipate, cobalt glutarate and cobalt succinate.

6. The process according to claim 1, wherein the at least one chromium compound soluble in the reaction medium is selected from the group consisting of chromium chloride, chromium bromide, chromium nitrate, chromium carboxylates and mineral and organic chromic acid salts.

7. The process according to claim 1, wherein the at least one iron compound soluble in the reaction medium is selected from the group consisting of iron chloride, iron bromide, iron nitrate, and iron carboxylates.

8. The process according to claim 1, wherein the catalyst also includes a soluble zirconium or hafnium compound.

9. The process according to claim 8, wherein the zirconium compound which is soluble in the reaction medium is selected from the group consisting of zirconium chloride, zirconium bromide, zirconium nitrate and zirconium carboxylates.

10. The process according to claim 8, wherein the hafnium compound which is soluble in the reaction medium is selected from the group consisting of hafnium chloride, hafnium bromide, hafnium nitrate and hafnium carboxylates.

11. The process according to claim 1, wherein the molar ratios between the manganese and/or cobalt, the chromium and the iron are between 1/0.001/0.001 and 1/10/10.

12. The process according to claim 1, wherein the amount of catalyst, expressed as a weight percentage of metal elements relative to the reaction mixture, is between 0.0001% and 5%.

13. The process according to claim 1, wherein the liquid reaction medium contains a solvent selected from the group consisting of aliphatic carboxylic acids having from 2 to 9 carbon atoms, perfluoroalkylcarboxylic acids, alcohols, halogenated hydrocarbons, ketones, lower alkyl esters of carboxylic acids and perfluoroalkylcarboxylic acids, tetramethylene sulphone (or sulpholane) and acetonitrile.

14. The process according to claim 1, wherein the solvent used is acetic acid.

15. The process according to claim 1, wherein the solvent represents from 1% to 99% by weight of the reaction medium.

16. The process according to claim 1, wherein the compound being oxidized is cyclohexane.

17. The process according to claim 1, wherein the gas comprising oxygen is selected from the group consisting of air, oxygen-enriched, oxygen-depleted air and oxygen diluted with an inert gas.

* * * * *